(12) United States Patent
Leko

(10) Patent No.: US 7,318,940 B2
(45) Date of Patent: Jan. 15, 2008

(54) **METHOD FOR ISOLATION OF SILYMARIN FROM *SYLIBUM MARIANUM* SEEDS**

(76) Inventor: Vladimir Leko, Istarska 7, Pozega (HR) 34000

( * ) Notice: Subject to any disclaimer, the term of this patent is extended or adjusted under 35 U.S.C. 154(b) by 280 days.

(21) Appl. No.: 10/533,073

(22) PCT Filed: Sep. 5, 2003

(86) PCT No.: PCT/HR03/00049

§ 371 (c)(1),
(2), (4) Date: Apr. 28, 2005

(87) PCT Pub. No.: WO2004/039386

PCT Pub. Date: May 13, 2004

(65) Prior Publication Data

US 2006/0159785 A1   Jul. 20, 2006

(30) Foreign Application Priority Data

Oct. 29, 2002   (HR) .......................... P 20020858 A

(51) Int. Cl.
*A61K 36/00* (2006.01)

(52) U.S. Cl. ...................................... 424/776; 424/725

(58) Field of Classification Search ..................... None
See application file for complete search history.

(56) References Cited

U.S. PATENT DOCUMENTS

| 3,773,932 A | * | 11/1973 | Madaus ....................... 514/456 |
| 4,368,195 A | | 1/1983 | Madaus |
| 4,895,839 A | * | 1/1990 | Bombardelli ................. 514/78 |
| 6,262,019 B1 | * | 7/2001 | Keller et al. .................... 514/2 |
| 6,309,678 B1 | | 10/2001 | Tandon |
| 7,172,774 B2 | * | 2/2007 | Leko ........................... 424/764 |

FOREIGN PATENT DOCUMENTS

| DE | 2017789 | * | 10/1971 |
| DE | 112261 | * | 4/1975 |

* cited by examiner

*Primary Examiner*—Christopher R. Tate
(74) *Attorney, Agent, or Firm*—St. Onge Steward Johnston & Reens LLC

(57) ABSTRACT

This invention relates to a method for the isolation of silymarin from *silybum marianum* seeds without precooling wherein the ground seeds are defatted using a hydrocarbon solvent, followed by extraction with a nontoxic medium polarity solvent, purification of the dried extract and drying of the crystals thus obtained.

24 Claims, No Drawings

METHOD FOR ISOLATION OF SILYMARIN FROM *SYLIBUM MARIANUM* SEEDS

METHOD FOR ISOLATION OF SILYMARIN FROM SYLIBUM MARIANUM SEEDS

Silymarin is a term for a complex composition of compounds: silybin, isosilybin, silydianin, silychristin, taxifolin, and kvercetin. The most significant natural source of silymarin is the seeds of *Slybum marianum*. Silymarin has been proven to be extremely hepatoprotective and it is a significant active substance in numerous herbal drugs. The most significant silymarin component is sylibin whereas the other components are present in smaller amounts. Most of the studiesof silymarin pharmacology relate to the activities of the whole composition whereas the pharmacological activities of the individual silymarin components are not well-known. Due to this reason, the production of silymarin is directed to the isolation from the seeds of *Silybum marianum* and further processing into a stabile crystalline form, silymarin thus obtained is suitable for production of various pharmaceutical forms in the domains of herbal medicines or dietetics.

According to the process described in U.S. Pat. No. 6,309,678, the isolation of silymarin includes cooling the seeds to −20° C., prior to milling. Powdered seeds are then extracted using n-hexane as the solvent for defatting. The resulting defatted seeds are further extracted with acetonitrile at room temperature. By evaporation of acetonitrile extract, a material is formed that has to be further purified by extraction with dichloromethane and the product, silymarin, is obtained by redissolving the residue in minimal amount of acetonitrile and precipitating silymarin by the addition of distilled water.

The described process includes an unacceptable precooling of the seeds to −20° C. prior to defatting. Described extracting of defatted material includes consumption of about 890 ml of acetonitrile for 100 g of the seeds (ratio 1:8.9, m/V) which is quite unacceptable for the industrial scale. Apart from this, acetonitrile is significantly toxic. By evaporation of the acetonitrile extract, such material is obtained that obviously contains some residual oil and requires further washing with dichloromethane. Dichloromethane is a bad choice of solution for the above mentioned purpose because it is significantly toxic and its boiling point is very low, resulting in great losses on industrial scale. Purification of silymarin by precipitating it with water from acetonitrile solution might be problematic because it can extract a product of high purity and color but resin-like consistency.

The process described in the document U.S. Pat. No. 4,368,195, just as its numerous versions, has been examined in laboratory because it was assumed that ethyl acetate was more appropriate solution than acetonitrile, due to its lower price and toxicity. The process includes defatting of the seeds by cold pressing. Such defatted residue is extracted several times (3.times) in boiling ethyl acetate. The ethyl acetate extract thus obtained is evaporated and the resulting residue is processed by a three-component extraction of water/methanol/dichloromethane wherein the residual oil passes into the dichloromethane fraction and silymarin remains within the aqueous-methanolic fraction. By evaporation of the aqueous-methanolic fraction the crude product is obtained which is further purified by precipitating it from methanolic solution, by adding distilled water.

The described process includes cold pressing of the seeds which has its technological advantages. However, a substantial part of the oil is left in the residue so that the ethyl acetate extract contains a lot of oil, apart from silymarin. The oil can be removed only by a three-component extraction. Furthermore, the process requires application of a large volume of ethyl acetate for the mass of the seeds, 3.times. 1:10 m/V which is non-economic on an industrial scale. Furthermore, a three-component extraction requires the application of a large amount of toxic organic solvents, such as dichloromethane and methanol, whose regeneration level is questionable. Furthermore, silymarin lags in aqueous-methanolic fraction evaporation of which requires a relatively large amount of energy, wherein stability of dissolved silymarin is questionable in the final phase of evaporation when the substance is exposed to relatively high temperatures in an aqueous medium, in which the solubility of oxygen from the air is far higher than the solubility in organic solvents. Additional purification of silymarin by way of precipitating it from a methanolic solution by adding distilled water might be problematic as in the previous process because the product can be extracted in resin-like consistency.

It has been concluded that both processes are not (at least in the described form) suitable for industrial isolation of silymarin from the seeds.

A new method for the isolation of silymarin and oil from the seeds has been developed. The method includes grinding the seeds, extraction of oil via a hot defatting process and extraction of defatted seeds with a medium polarity solvent. After filtration, the extract is evaporated to dryness and the residue is azeotropically dried. The dried extract is then further defatted in hot ether wherein, after the chilling, filtration and drying, a concentrate of silymarin in the form of a homogeneous yellow-orange crystalline substance is obtained having a high melting point (ca. 140-165.degrees. C.). Yield of silymarin is 2.0-2.5% according to the content of total silymarin of 86-97% and approx. 20% of the oil calculated by a crude seed.

In comparison with the previously described methods, the process described in the instant invention does not use the toxic solvents, dichloromethane, methanol or acetonitrile. The described method applies acetone as the least toxic and by far the cheapest medium polarity solvent. The method is developed for the use of minimal (optimum) amounts of organic solvents with a regeneration rate of approx. 90-95%. All chemicals and technological details are stated in the detailed description of the method. The method comprises the following steps:

1. grinding the seeds of *Slybum marianum*
2. extracting the seed powder as a means for defatting
3. filtering the defatted seed powder
4. extraction of the defatted seed powder with acetone
5. filtration of the extracted seed powder
6. evaporation of the acetone extract filtrate
7. azeotropic drying of the extract with toluene
8. secondary defatting of the extract with diisopropyl ether
9. filtration of the resulting silymarin crystals
10. drying of the silymarin crystals under vacuum Crude seeds of *Sylbum marianum* are powdered using a jet mill with rotating blades with the application of screens up to 40 mesh. After this, defatting of the resultant seed powder is conducted by extraction with a solvent suitable for defatting, such as a hydrocarbon. In one preferred practice of this invention, n-hexane is used as the hydrocarbon solvent. In another preferred practice of this invention, petroleum ether is used. A suspension of the seed powder in the applied ratio of seed powder:solvent (m/V) can normally be stirred with a mechanical stirrer.

The filtration is conducted in via vacuum filtration. The filtrate has intense yellow color and contains the oil of the seeds in n-hexane. The filtered powder is then heated under vacuum at 70° C. for 2-3 hours to provide complete removal of extraction solvent traces According to this invention, defatted seeds do not need to be further dried in order to rid them of the traces of absorbed n-hexane but rather are extracted with a medium polarity solvent, such as acetone, immediately after vacuuming.

Extraction with acetone is conducted at a temperature of between 18° C. and 56° C. Optimum extraction time is approx. from 24 to 72 hours, depending on the temperature at which the extraction is conducted. Filtration follows the extraction.

In another version of the invention, defatting is conducted in common percolator at room temperature during at least 48 hours. After defatting and removal of traces of n-hexane, percolation with acetone for isolation of silymarin is continued.

Azeotropic distillation follows, by which water and toluene is removed from the residue after evaporation of the acetone filtrate After evaporation of acetone in the filtrate, a mixture of toluene and water is collected. The toluene and water mixture is easily separated in an extractor and 80% of the used toluene is regenerated. A vacuum system is used to provide drying at a temperature as low as possible.

For purification, i.e. removing the residual oil, according to the invention ethers are applied as a means of extraction. According to the invention, ethers with 4 to 8 carbon atoms such as tetrahydrofuran, or diisopropyl ether, or diethyl ether are appropriate for secondary defatting.

It has been found that diisopropyl ether acts as the most efficient solvent for defatting the extracts wherein the oil is completely dissolved while silymarin constituents remain almost completely suspended. One part of the evaporated residue can stay attached to the walls of the extraction flask and it is not removed spontaneously during heating at the reflux temperature of the solvent. Therefore, mechanical stirring is needed. On an industrial scale, a reactor with mechanical mixer whose shape follows the geometry of the extraction flask is used. The purpose of it is to avoid the silymarin getting glued to the walls during azeotropic drying with toluene. Once formed, the suspension of silymarin constituents is nicely defatted and easily filtered in vacuo after the cooling. Further cooling of the suspension does not substantially affect the level of product purity, since the solubility of silymarin constituents in diisopropyl ether is extremely low. The next example severs only as an illustration of the invention and is not meant to be used for defining the range and content of the invention.

THE EXAMPLE 400.00 g of ground *Sylbum marianum* seeds were weighted in a 2000 ml three-necked flask and 1200 ml of n-hexane was added. The suspension thus obtained was heated with stirring using a mechanical mixer and heated to reflux during 30 minutes. The refluxing suspension was stirred for an additional 3 hours. After cooling, the herbal material was vacuum filtered using a Buchner funnel. The flask was then washed with n-hexane (2×100 ml) The remaining seed powder was further washed with n-hexane (2×100 ml). Approx. 1500 ml (about 95% of the whole amount of the used n-hexane) of n-hexane was distilled from the filtrate leaving a residual pale yellow oil which was heated at 70° C. in vacuum, at 8-10 mbar, during 2 hours to remove any remaining traces of hexane. A clear yellow-orange oil of weak characteristic scent was obtained:

BATCH-1: 60.05 g (15.0%, calculated by weight of the crude seed)

BATCH-2: 61.41 g (15.4%, calculated by weight of the crude seed)

BATCH-3: 61.98 g (15.5%, calculated by weight of the crude seed) The defatted *Sylbum marianum* seeds (approx. 340 g) were then removed into the 2000 ml three-necked flask and 1200 ml of acetone was poured into it, and the obtained suspension was stirred with a mechanical mixer at the room temperature during 72 hours. After this, the suspended herbal material was vacuum filtered through a Buchner funnel. The filtered material was then twice washed, each time with two 100 ml portions of acetone. From the obtained yellow filtrate (approx. 1550-1580 ml), acetone was removed by distillation at the atmosphere pressure, wherein approx. 1550-1530 ml (93.8-95.6%) of the whole amount was regenerated.

After removal of the acetone was complete, 60 ml of toluene was added and the resulting solution was evaporated in a rotating evaporator at a temperature of 80-85° C. and a pressure of 50-60 bar, wherein 25-27 g (6.25-6.75 g) of dry extract was obtained in form of yellow-orange crystals, mottled with yellow-orange oil. 50 ml of diisopropyl ether was added to the dry extract and with stirring heated to the temperature at which the solvent refluxed, approx. 67-69° C., during 25-30 minutes. Heating was continued for an additional 30 min. after which the suspension was allowed to cool to the room temperature during approx. 1 hour. The resulting crystals were then filtered and washed with 2.times with 25 ml portions of cold diisopropyl ether. The product was dried in a vacuum drier at 40° C. and the pressure of 8-10 mbar, during 24 hours. Silymarin (1), in form of small shiny crystals, with the color ranging from yellow to light orange, was obtained. [0021] BATCH-1: 8.52 g (2.13%), t. t. 142.2-165.0° C. [0022] BATCH-2: 9.02 g (2.26%), t. t. 143.0-164.2 C [0023] BATCH-3: 8.91 g (2.23%), t. t. 140.2-161.1° C. From the yellow diisopropyl ether filtrate, after the filtration of silymarin (approx. 100 ml) by distillation at the atmospheric pressure, 95-96 ml (95-96%) of diisopropyl ether was regenerated. The residue was dried in vacuum at 8-10 mbar with heating at 70° C., during 2 hours wherein a second batch of yellow-orange oil was obtained. The oil was to be further filtered to be rid of traces (less than 1%) of insoluble material suspended in the diisopropyl ether.

BATCH-1: 17.84 g (4.46%, calculated by weight from the crude seed)

BATCH-2: 17.23 g (4.31%, calculated by weight from the crude seed)

BATCH-3: 18.70 g (4.68%, calculated by weight from the crude seed)

The total of obtained oil: (primary+secondary)

BATCH-1: 77.89 g (19.5%, calculated by weight from the crude seed)

BATCH-2: 78.64 g (19.7%, calculated by weight from the crude seed)

BATCH-3: 80.86 g (20.2%, calculated by weight from the crude seed) Optimum conditions of drying of silymarin have been stated. Due to its phenolic components, silymarin is sensitive to oxygen and light. The state method enables successful drying of silymarin because after it is filtered, it contains only trace amounts of absorbed diisopropyl ether from which it is very easily dried.

Diisopropyl ether, acetone and n-hexane are regenerated to approx. 95% of their use and can be reused. Commercial diisopropyl ether is stabilized with approx. 50 ppm of antioxidant, such as 2,6-di-terc-buthil-4-methylphenol (BHT), however, solvent which is regenerated after distillation will not contain a stabilizer. In case of frequently repeated application of the same diisopropyl ether, solvent as such can be used without problems if stored for short periods of time in well sealed barrels. For long storage periods, BIT is to be added to the regenerated solvent, approx. 5 g per 100.1.

Silymarin obtained by the described method is a crystal-like matter of orange color, without scent, and melts at a temperature range between 140 and 165° C.

In silymarin IR-spectrum, a characteristic stretching band of alcoholic and phenol O—H bonds at 3400, and ketone stretching band at about 1640 cm are visible.

IR (KBr) v: 3401 (O—H, phenol group), 2928, 1745, 1641 (c.dbd.O, keto-group), 1513, 1465, 1358, 1275, 1160, 1160, 1083, 1027, 992, 813, 782, 644 cm.

In IR spectrum of *Silybum marianum* oil the band appears at about 1744 cm. It is characteristic for stretching of an ester carbonyl.

IR (film) v: 3009, 2926, 2855, 1744 (C.dbd.O, ester group), 1656, 1466, 1418, 1378, 1239, 1163, 1099, 914, 723 cm.

Qualitative (IR spectrum, thin-layer chromatography) and quantitative (spectrophotometry) analysis were conducted on the obtained silymarin.

Quantitative analysis of silymarin concentrate obtained by the described method was done spectrophotometrically with the use of 2,4.dinitrophenylhydrazine (DNPH) as reagent, by the method described in the literature (H. Wagner, P. Diesel, M, Seitz, Arzneim. Forsch. (Drug Res.) 24 (1974) 466-471). The results are in Table 1. TABLE-US-00001 TABLE 1. The results of quantity content of the total silymarin in silymarin samples, batches 1, 2 and 3, obtained according to the described method. Calculated absorption measured per SYLIM. TOTAL SAMPLE weight absorption 50.00 mg. subs. (%).sup.1 Silibyn-stand.sup.2 0.05044 0.237 0.235 100 Silymarin, B-1 0.05043 0.214 0.212 90.21 Silymarin, B-2 0.05002 0.203 0.203 86.38 Silymarin, B-3 0.05010 0.227 0.227 96.60.sup.1 The content of total silymarin presents the content of total ketone, i.e., all the silymarin components with ketone functionally (so called DNPH of positive compounds). .sup2. A standard of silymarin prepared by preparatory chromatography was declared as 100% silymarin.

The invention claimed is:

1. A method for the isolation of silymarin from—*Silybum Marianum* seeds without precooling the seeds, comprising the following steps:
   a) grinding the seeds to a fine powder, whereby the seeds have not been precooled prior to grinding;
   b) defatting the pulverized seeds with a hydrocarbon solvent
   c) extraction of the defatted seeds with a medium polarity solvent at a temperature from 18 to 56° C. in order to obtain a silymarin extract;
   d) evaporation of solvent from the silymarin extract;
   e) removal of water from the evaporation residue from step d) to form a dried crystalline silymarin extract;
   f) purification of the dried crystalline silymarin extract to remove residual oils by washing and drying of the dried crystalline silymarin extract.

2. The method for isolation of silymarin from *Silybum marianum* of claim 1, characterized by the fact that the step of grinding is done in a mill comprising—rotating knives and screen of 40 mesh or less.

3. The method for isolation of silymarin from *Silybum marianum* seeds of claim 1, characterized by the fact that the ground seeds are transferred into a reactor with mechanical mixer whose form is following geometry of the reactor vessel.

4. The method for isolation of silymarin from *Silybum marianum* seeds of claim 3, characterized by the fact that the step of defatting is done in an extractor at the temperature at which the hydrocarbon solvent boils.

5. The method for isolation of silymarin from *Silybum marianum* seeds of claim 1, characterized by the fact that in step b) defatting is done in percolator at room temperature.

6. The method for isolation of silymarin from *Silybum marianum* seeds of claim 1, characterized by the fact that hexane or petroleum ether are used as solvents for defatting.

7. The method for isolation of silymarin from *Silybum marianum* seeds of claim 6, characterized by the fact that n-hexane is used as the solvent for defatting.

8. The method for isolation silymarin from *Silybum marianum* seeds of claim 7, characterized by the fact that the ratio between the seeds and n-hexane is from 1:2 to 1:5 m/V.

9. The method for isolation of silymarin from *Silybum marianum* seeds of claim 7, characterized by the fact that the ratio between the seeds and n-hexane is 1:3 m/V.

10. The method for isolation of silymarin from *Silybum marianum* seeds of claim 1, characterized by the fact that acetone is used as the medium polarity solvent for the extraction of defatted seeds.

11. The method for isolation of silymarin from *Silybum marianum* seeds of claim 1, characterized by the fact that the extraction of defatted seeds is done in an extractor during 24 hours, at the approx. temperature at which acetone boils.

12. The method for isolation of silymarin from *Silybum marianum* seeds of claim 1, characterized by the fact that the extraction of defatted seeds is done in percolator during 72 hours, at room temperature.

13. The method for isolation of silymarin from *Silybum marianum* seeds of claim 10, characterized by the fact that the ratio between the seeds and acetone is from 1:2 to 1:5 m/V.

14. The method for isolation of silymarin from *Silybum marianum* seeds of claim 10, characterized by the fact that the ratio between the seeds and acetone is 1:3 m/V.

15. The method for isolation of silymarin from *Silybum marianum* seeds of claim 1, characterized by the fact that the medium polarity solvent is acetone and the evaporated acetone residue is dried by azeotropic distillation with toluene.

16. The method for isolation of silymarin from *Silybum marianum* seeds of claim 1, characterized by the fact that the separation of the residual oil from the dried extract be done using ethers of between 4 and 8 carbon atoms.

17. The method for isolation of silymarin from *Silybum marianum* seeds of claim 16, characterized by the fact that purification of silymarin is done at the boiling temperature of the ether used.

18. The method for isolation of silymarin from *Silybum marianum* seeds of claim 16, characterized by the fact that the separation of the dried extract is done with tetrahydrofuran, diisopropyl ether or diethyl ether.

19. The method for isolation of silymarin from *Silybum marianum* seeds of claim 18, characterized by the fact that the separation of the dried extract is done with diisopropyl ether at the temperature of approx. 67 to 69° C., during 25 to about 30 minutes.

20. The method for isolation of silymarin from *Silybum marianum* seeds of claim 1, characterized by the fact that suspension is cooled to room temperature, during 1 hour.

21. The method for isolation of silymarin from *Silybum marianum* of claim 1, characterized by the fact that crystales of purified silymarin are filtered and washed several times with diisopropyl ether.

22. The method for isolation of silymarin from *Silybum marianum* seeds of claim 1, characterized by the fact that product is dried in drying section.

23. The method for isolation of silymarin from *Silybum marianum* seeds of claim 1, characterized by the fact that product is dried at increased temperature and decreased pressure.

24. The method for isolation of silymarin from *Silybum marianum* seeds of claim 23, characterized by the fact that product is dried at 40 degrees. C. and a pressure of 8 to about 10 mbar.

* * * * *